(12) United States Patent
Hsu

(10) Patent No.: US 10,377,982 B1
(45) Date of Patent: Aug. 13, 2019

(54) CULTIVATION BAG FOR CULTIVATING MICROBES

(71) Applicant: Wei K. Hsu, Plano, TX (US)

(72) Inventor: Wei K. Hsu, Plano, TX (US)

( * ) Notice: Subject to any disclaimer, the term of this patent is extended or adjusted under 35 U.S.C. 154(b) by 0 days.

(21) Appl. No.: 16/238,410

(22) Filed: Jan. 2, 2019

(51) Int. Cl.
  *C12M 1/00* (2006.01)
  *C12M 1/12* (2006.01)
  *C12M 1/04* (2006.01)
  *A01G 18/64* (2018.01)

(52) U.S. Cl.
  CPC .............. *C12M 23/14* (2013.01); *A01G 18/64* (2018.02); *C12M 23/24* (2013.01); *C12M 25/00* (2013.01)

(58) Field of Classification Search
  CPC ................................ C12M 23/14; A01G 18/64
  See application file for complete search history.

(56) References Cited

U.S. PATENT DOCUMENTS

| | | | | |
|---|---|---|---|---|
| 3,865,695 A | * | 2/1975 | Massier | C12M 23/14 435/256.8 |
| 4,878,312 A | * | 11/1989 | Shimizu | A01G 18/64 47/1.1 |
| 4,977,702 A | | 12/1990 | Fortin et al. | |
| 5,230,430 A | * | 7/1993 | Kidder | B65D 81/24 206/484.1 |
| 5,659,997 A | | 8/1997 | Sprehe et al. | |
| 6,358,731 B1 | | 3/2002 | Hsu | |
| 7,066,337 B2 | | 6/2006 | Hsu | |
| 8,001,718 B2 | * | 8/2011 | Vandenhove | A01G 18/64 47/1.1 |
| 9,386,751 B2 | * | 7/2016 | Creekmore | C12N 1/14 |
| 2009/0197327 A1 | * | 8/2009 | Bergmann | A01G 18/64 435/297.1 |
| 2015/0000188 A1 | * | 1/2015 | Shirahane | A01G 18/64 47/1.1 |

* cited by examiner

*Primary Examiner* — Jonathan M Hurst
(74) *Attorney, Agent, or Firm* — Grady K. Bergen; Griggs Bergen LLP

(57) ABSTRACT

A cultivation bag assembly for the cultivation of microbes, fungi and other organisms includes a bag having first and second walls joined along side edges to define a bag interior for containing a food substrate and an organism to be cultivated. At least one of the first and second walls is constructed of a layer of water-vapor permeable material to allow the passage of water vapor therethrough. A bag wall overlay layer formed from gas impermeable layer is releasably coupled to the bag. The overlay layer overlays the layer of water-vapor permeable material to prevent the passage of gases therethrough. The bag wall overlay layer has an opening with a gas filter patch covering the opening to allow the passage of oxygen and carbon dioxide gases through the gas filter patch to and from ambient air to facilitate incubation of the organism within the interior of the bag. The bag wall overlay layer is removable from the bag to allow water vapor to pass through the layer of water-vapor permeable material to ambient air facilitate drying of the bag contents after incubation is complete.

20 Claims, 7 Drawing Sheets

CULTIVATION BAG FOR CULTIVATING MICROBES

FIELD OF THE INVENTION

The invention relates to cultivation bags for the cultivation of microbes, fungi, and other organisms, their manufacture and use.

BACKGROUND

With higher demand for organic products, methods for increasing the production of crops without the use of chemical fertilizers, pesticides and herbicides has been of particular interest and importance. Biopesticides used for agricultural purposes have been developed and continue to be developed to control pests and weeds, as well as act as fertilizers, thus increasing plant growth and crop yields without the need for chemicals that can damage the environment and cause safety and/or health concerns. These biological control agents are typically in the form of natural microbes, fungi, or other organisms, and in particular, fungi mycelium. These biological agents have a toxic effect on harmful insects and/or weeds, but do not negatively affect the growing crops, and/or may act beneficially as fertilizers that actually promote the growth of plants with which they are used.

The particular biological control agents used as pesticides act as parasitic microbes that attack the insects or undesirable plant matter causing them to die. By spreading these microbes or biological agents in the soil and fields, these materials can naturally destroy the damaging insects and/or weeds, as well as act as fertilizing agents to facilitate crop growth. Research and development is still underway in determining and isolating effective microbes and biological agents out of the many thousands that exist for use as such pesticides. Therefore their use is only expected to increase over time.

Of those parasitic microbes and organisms that are discovered and isolated for use as biopesticides, they must be produced in large quantities so that they can be used commercially for agricultural purposes. Once such system that is used by large industries involves produces the organisms in bulk. This involves the use of a large vessel containing a substrate. The substrate is a nutrient food source that a microbe, fungi, or particular organism prefers and when introduced into this substrate will tend to grow particularly rapidly on such substrate. In order to be used for cultivation the substrate must be sterilized to eliminate the growth of other undesirable microbes. To do this, the vessel with the substrate is typically heated to ≥121° C. for a certain length of time. This is typically accomplished with the use of live steam. The amount of time for sterilization depends on the amount of substrate being sterilized. After sterilization, the vessel and substrate are cooled. The pure, isolated microbe or biological agent, such as fungi mycelium, which may be previously grown in petri dishes or test tubes are then added to the substrate within the vessel. The vessel then slowly rotates and mixes the materials until they are homogenously mixed together.

Once the materials are mixed, the mixture is introduced into bags in suitable amounts and allowed to incubate at a desired temperature and humidity to promote growth of the particular microbes or other organisms. Incubation is typically complete when the substrate is completely consumed. Incubation is ended by drying the bag contents, which typically occurs under vacuum. After drying, the resulting dried microbial material is crushed and reduced in size to desired particles sizes.

While the large bulk processing systems are useful in producing large quantities of microbial materials useful as biopesticides, they have shortcomings. Such bulk systems are expensive and difficult to use, making them practical only for large producers. Furthermore, the bulk vessel is susceptible to contamination. If even one contamination spore enters the bulk vessel after sterilization, such as during introduction of the desired microbe that is being cultivated, the whole batch may be rendered unusable.

A more affordable method that can be used by smaller producers does not make use of a bulk vessel. Instead smaller plastic bags filled with substrate are used that can withstand the temperatures of sterilization (i.e., ≥121° C.) for a sufficient amount of time to sterilize the substrate. The bags may have a small filter to allow steam used for sterilization to escape during the sterilization procedure so that the bag does not explode or burst as it is heated. If no filter is used, the bag may be positioned upright with one end of the bag being open but with the opening restricted with either a foam or cotton wool material to allow the escape of steam.

Once the sterilized substrate is cooled, pure microbes or organisms to be cultivated are introduced into the bag. If a filtered bag is used, the open end is sealed, such as by welding. The bag and its contents are then agitated to mix the materials and the bag is placed on a shelf for incubation.

After incubation, the bag is cut open and the contents are poured into a second drying bag. Drying typically occurs with dry heating under a vacuum within a vacuum chamber for increased efficiency. Drying in bags is more suitable than in industrial drying, which involves higher temperatures, which can kill off the microbes that have been cultivated. The drying bag must be constructed to allow water vapor to readily escape while retaining the bag contents within the bag. Thus, the drying bag must have a large area of filter material to allow the water vapor to escape efficiently and quickly. The requirement of needing a second drying bag, however, adds additional costs and labor, as the ripe microbes from the incubation bag must be transferred to the drying bag to facilitate drying.

To overcome the shortcomings of the above-described methods, improvements are needed.

BRIEF DESCRIPTION OF THE DRAWINGS

For a more complete understanding of the disclosure, reference is now made to the following descriptions taken in conjunction with the accompanying figures, in which.

DETAILED DESCRIPTION

Figure 1:
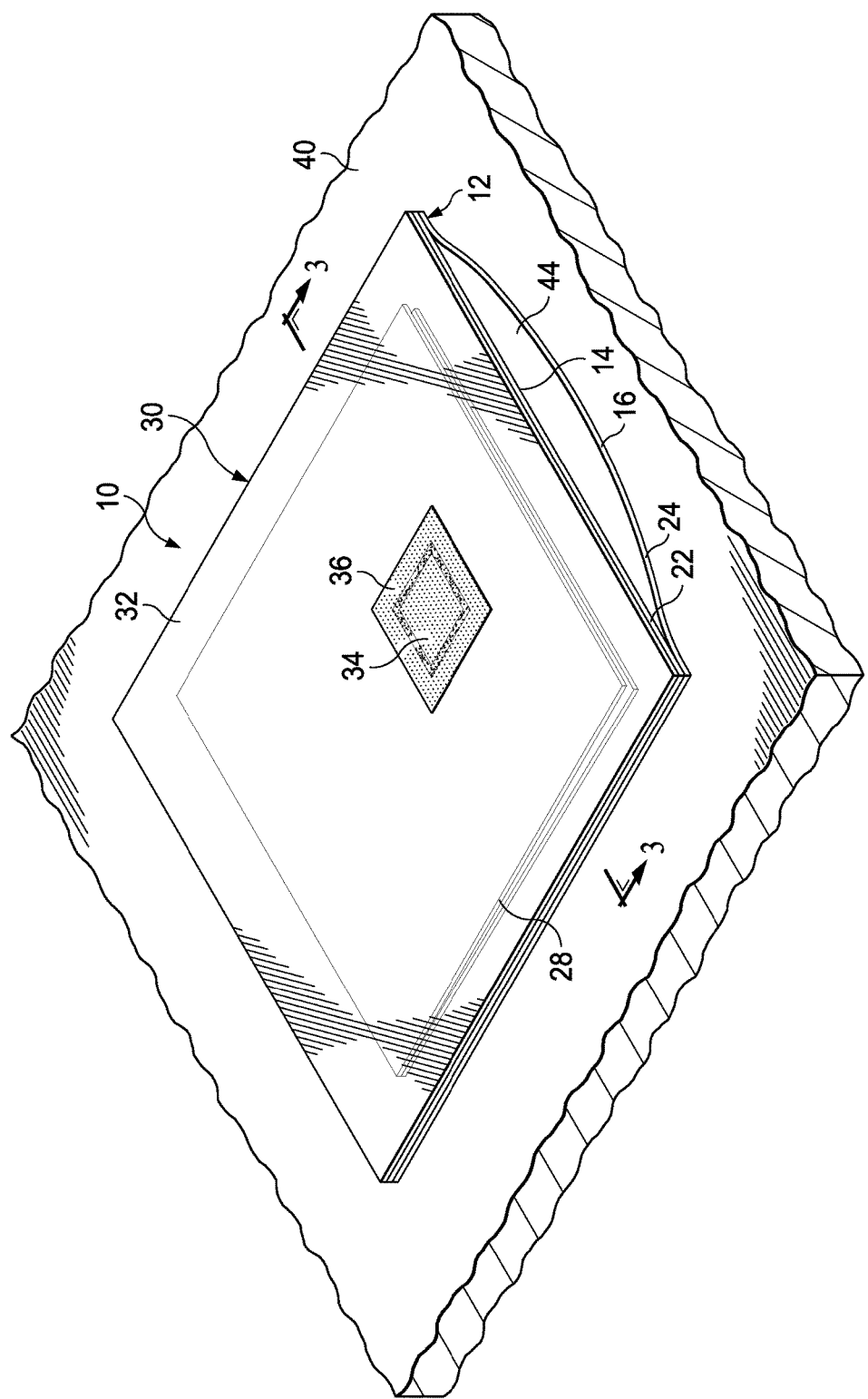
FIG. 1 is a top and left perspective view of a cultivation bag assembly shown constructed in accordance with particular embodiments of the invention.

The control of pests by interference with their ecological status is achieved by introducing a natural enemy or a pathogen into the environment. This is also called biocontrol. In simple terms, parasites and agents that cause sickness to pests are introduced into the pests by natural means and cause the pests to die. The present invention is related to an improved cultivation bag that has many advantages over the present art to reduce the steps in preparation and manufacture of these agents and to reduce risks of competing or contaminating matter introduced into to the process.

The bag assemblies of the invention are useful in cultivation through solid state fermentation. Solid state fermentation (SSF) can be defined as the growth of microorganisms in a moist solid substance in the absence of liquid water. The substance or substrate usually is composed of grain or grain waste, with addition of sugar, corn grits, rice wheat waste, potato waste. etc., which mimic the natural environment which the biological control agents grow in nature. SSF simulates the living conditions of filamentous fungi and is the biotechnological process of choice. Under favorable conditions, spore germination takes place through the formation of tubes which grow and will be the base of future mycelium. Through this process mycelium and spore production become the biocontrol agent. This agent infects and kills the pests once it is introduced into their environment.

As filamentous fungi grow hypha, which are the branching filaments that mycelium of the fungi, penetrate into the solid matrix, becoming impossible to separate substrate from mycelium. The biomass thus formed becomes the product to be dried and reduced in size so that it can be easily sprayed into fields or areas where the pests to be destroyed live. Most of the time this will be on vegetation that humans plant in agriculture. It is therefore an advantage to stimulate maximum growth of filamentous fungi spores by allowing wet substrate contained in a bag and providing a breathing means through a filter. The filter is designed to allow gas exchange between the filamentous fungi in the substrate and ambient air by expelling $CO_2$ (carbon dioxide) generated in the bag and breathing in $O_2$ (oxygen). The filter will also have small enough pores to obstruct contaminating living matter to enter the bag and thus to consume and share the nutrients in the substrate. The amount of $CO_2$ in the bag is critical to optimum growth of filamentous fungi.

By placing the incubating bag under controlled conditions of temperature, ventilation, humidity and nutrients used, the substrate mass is totally consumed by the cultivated biological control agent. When the substrate mass is fully consumed, the bag contents are dried. In the prior art methods, this is done by removing the mass from the incubation bag and introducing it into a drying bag. The present invention eliminates this stage, however, since the incubation and drying bag is the same bag.

In the drying process, drying air may be introduced into the environment and the large physical area of an underlying filter material allows rapid dehydration of the biomass in the bag. When drying is completed, the bags is opened and the dried bio mass is reduced into particles that are further size reduced for packaging and marketing.

Referring to FIG. 1, a cultivation or incubation bag assembly 10 is shown for cultivating and drying microbes, fungi and other organisms, such as fungi mycelium, as discussed. The various components of the cultivation bag assembly 10 and its construction can be seen more readily in FIGS. 2 and 3.

As shown in FIGS. 2 and 3, the bag assembly 10 includes multiple layers of material that are joined together to form the bag assembly 10. The bag assembly includes a drying bag 12 having upper and lower walls 14, 16 joined around their perimeters along left, right and rear side edges, such as at joint or seal 18 (FIG. 3) to define a bag interior 20 between the walls 14, 16. The front of the bag 12 may initially be open to allow for the introduction of a substrate material and a microbe, fungi, or other organism to be cultivated.

The walls 14, 16 may each be constructed from flexible top and bottom film layers 22, 24, respectively, each having a central opening 26. As shown, the central openings 26 may be rectangular in configuration, but may have other configurations as well. The openings 26 may make up from 50%, 55%, 60%, 65%, 70%, 75%, 80%, 85%, 90%, 95% or more of the total area circumscribed within the outer perimeter of the film layers 22, 24. The film layers 22, 24 may be gas impermeable so that water vapor and gases cannot readily pass through the material of the film. The film layers 22, 24 may be formed from thermoplastic film layers, such as the polyolefins of polypropylene or high density polyethylene (HDPE). In certain embodiments, the walls 14, 16 may be configured and joined together to provide gussets along the sides of the bag assembly 10 so that the bag assembly 10 constitutes a gusseted bag assembly.

It should be noted in the description, if a numerical value, concentration or range is presented, each numerical value should be read once as modified by the term "about" (unless already expressly so modified), and then read again as not so modified unless otherwise indicated in context. Also, in the description, it should be understood that an amount range listed or described as being useful, suitable, or the like, is intended that any and every value within the range, including the end points, is to be considered as having been stated. For example, "a range of from 1 to 10" is to be read as indicating each and every possible number along the continuum between about 1 and about 10. Thus, even if specific points within the range, or even no point within the range, are explicitly identified or referred to, it is to be understood that the inventor appreciates and understands that any and all points within the range are to be considered to have been specified, and that inventor possesses the entire range and all points within the range.

Positioned over the central openings 26 and joined to each of the top and bottom film layers 22, 24 to form the walls 14, 16 is a layer of gas and water-vapor permeable material 28. The water-vapor permeable material 28 is constructed to allow the passage or transmission of air and other gases, as well as water vapor through the material 28. This may be a non-woven polyolefin fiber material, such as that sold under the name TYVEK®, available from E. I. du Pont de Nemours and Company, Wilmington, Del. Examples of suitable commercially available products for the material 28 include, but are not limited to, TYVEK® 1025B, TYVEK® 1059B, and TYVEK® 1072B materials. The permeable material 28 may have a perm rating of from 5 or greater to facilitate the passage of water vapor through the material. In particular embodiments, the water vapor transmission through the layer 28 may range from at least, equal to, and/or between any two 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60 perms or more, in certain instance. The permeable material 28 may be suitable for filtering out particles having a particle size of from 0.2 micron to 1 micron. Thus, the permeable material 28 retains particles and powder of larger particle sizes within the bag 12.

The side edges of the permeable layers 28 are joined to the film layers 22, around the perimeter of the central opening 26 so that the opening 26 is completely covered by the permeable layer 28. In many applications, the material of the film layers 22, 24 and the water-vapor permeable layer 28 may be of the same thermoplastic or polyolefin material having the same or similar melting points, e.g., polypropylene or HDPE, so that they may be joined together through heat or ultrasonic welding so that the materials are non-releasably fused together or otherwise strongly joined together so that they are not easily separated. In other embodiments, other coupling means may be used to join the permeable layer 28 to the film layers 22, 24, such as through the use of a strong adhesive layer positioned between the materials.

Likewise the film layers 22, 24 are joined together around their outer perimeters along the left, right and rear side edges, such as at 18, and each layer 22, 24 may be of the same or similar thermoplastic material having the same or similar melting points, e.g., polypropylene or HDPE, so that they may be joined together through heat or ultrasonic welding so that the materials are permanently or non-releasably fused together or otherwise strongly joined together so that they are not easily separated. In other embodiments, other coupling means may be used to join the permeable layer 28 to the film layers 22, 24, such as through the use of a strong adhesive layer positioned between the materials. In many instances, the joint or seal where the permeable layers 28 are joined to the film layers 22, 24 will be offset from the joint or seal that joins the film layers 22, 25 together so that they are not coincidental or overlay one another. Having the joints or seals offset from one another in this way facilitates strengthening the bag 12.

In alternate embodiments, the bottom film layer 24 may be eliminated and the bottom wall 16 may be formed entirely of the permeable layer 28, which may be sized and configured to be joined along its side edges to the film layer 22. In still another variation, one or both of the film layers 22, 24 may be eliminated with the layer of permeable material 28 being used to form one or both of the walls 14, 16 of the bag 12. In cases where the permeable material 28 forms both walls 14, 16 of the bag 12.

The bag assembly 10 further includes at least one bag wall overlay layer 30. The overlay 30 may be constructed from of a film layer 32 that is gas impermeable so that water vapor and gases cannot readily pass through the material of the film. The film layer 32 may be formed from thermoplastic film, such as the polyolefins of polypropylene or HDPE. The film layer 32 is sized and configured to overlay the entire upper surface of the water-vapor permeable layer 28 of the upper wall 14 to prevent the passage of gases to and from the permeable layer 28 through the film 32.

An opening 34 is formed in the film layer 32 of the overlay 30 at a position so that the opening 34 directly overlays the permeable layer 28 of the upper wall 14 when joined thereto. The opening 34 is smaller in area than the permeable layer 28 so that only a portion of the permeable layer 28 underlies the opening 34.

A gas filter patch 36 is joined to the film layer 32 around its side edges and is used to cover the opening 34. The gas filter patch 36 is an incubation filter that allows the optimum gas exchange in the bag below it. This involves the passage of air and/or oxygen and carbon dioxide gases to and from ambient air, as well as some water vapor, to facilitate cultivation. The gas filter patch 36 may a non-woven polyolefin fiber material. There are many commercially available materials useful for the filter patch 36, which may be formed from non-woven polypropylene or HDPE. The filter patch material will typically have smaller openings than that used for the permeable layer 28. In particular applications, the filter patch 36 may be suitable for filtering out particles having a particle size of from 0.01 micron to 0.2 micron or greater. The filter patch 36 and the corresponding opening 34, in conjunction with the porosity of the filter patch 36, may be sized and configured to allow the selected passage of air, oxygen and carbon dioxide, and some water vapor, for the particular organism being cultivated. Thus, the size and configuration of the filter patch 36 and opening 34 may vary depending on the purpose, use, and environmental conditions (i.e., the type of organism being cultivated and its cultivating environment) of the bag assembly 10.

The side edges of the filter patch 36 are joined to the film layer 32, around the perimeter of the opening 34 so that the opening is completely covered by the filter patch 36. In many applications, the material of the film layer 32 and the filter patch layer 36 may be of the same thermoplastic or polyolefin material having the same or similar melting points, e.g., polypropylene or HDPE, so that they may be joined together through heat or ultrasonic welding so that the materials are permanently or non-releasably fused together or otherwise strongly joined together so that they are not easily separated. In other embodiments, other coupling means may be used to join the filter patch 36 to the film layer 32 to the film, such as through the use of a strong adhesive layer positioned between the materials.

In the embodiment shown, the bag overlay 30 is releasably coupled and sealed around its perimeter to the upper bag wall 14. This may be achieved by securing the side edges of the film layer 32 along the upper side edges of the upper film layer 22. In certain embodiments, this releasability may be achieved by utilizing different thermoplastic or polyolefin materials for each of the bag overlay film 32 and the upper film layer 22. This may be due, at least in part, due to different melting points or other properties of the materials. In certain embodiments, the difference in melting points between the different materials used to provide the releasability may be from 10° C., 20° C., 30° C., 40° C., 50° C. or more. Thus, for example, the bag overlay 30 and/or bag overlay film 32 may be constructed of polypropylene, which may have a melting point of from 130° C. to 171° C., while the upper film layer 22 may be formed from HDPE, which may have a melting point of from 115° C. to 135° C. The overlay film 32 and the upper film layer 22 of the bag 12 may be heat or ultrasonically welded together along their side edges. Because of the different materials used and their different melting points and/or properties, the materials are not as strongly held together as they would be if they were formed from the same materials. This low bonding strength aids or facilitates the releasability of the bag wall overlay 30 from the bag 12, as will be discussed later on. In other instances, the use of a releasable adhesive may be used to join and seal the bag overlay 30 to the upper bag wall. This may be a continuous layer of adhesive that effectively seals and releasably joins the layers together.

In the embodiment shown, only a single bag wall overlay 30 is used to cover the upper wall 14 of the bag assembly 10. In other embodiments, however, a second releasable bag wall overlay (not shown) constructed similarly to the bag overlay 30 may be used and be joined to the lower surface of the lower wall 16 of the bag 12.

Figure 2:
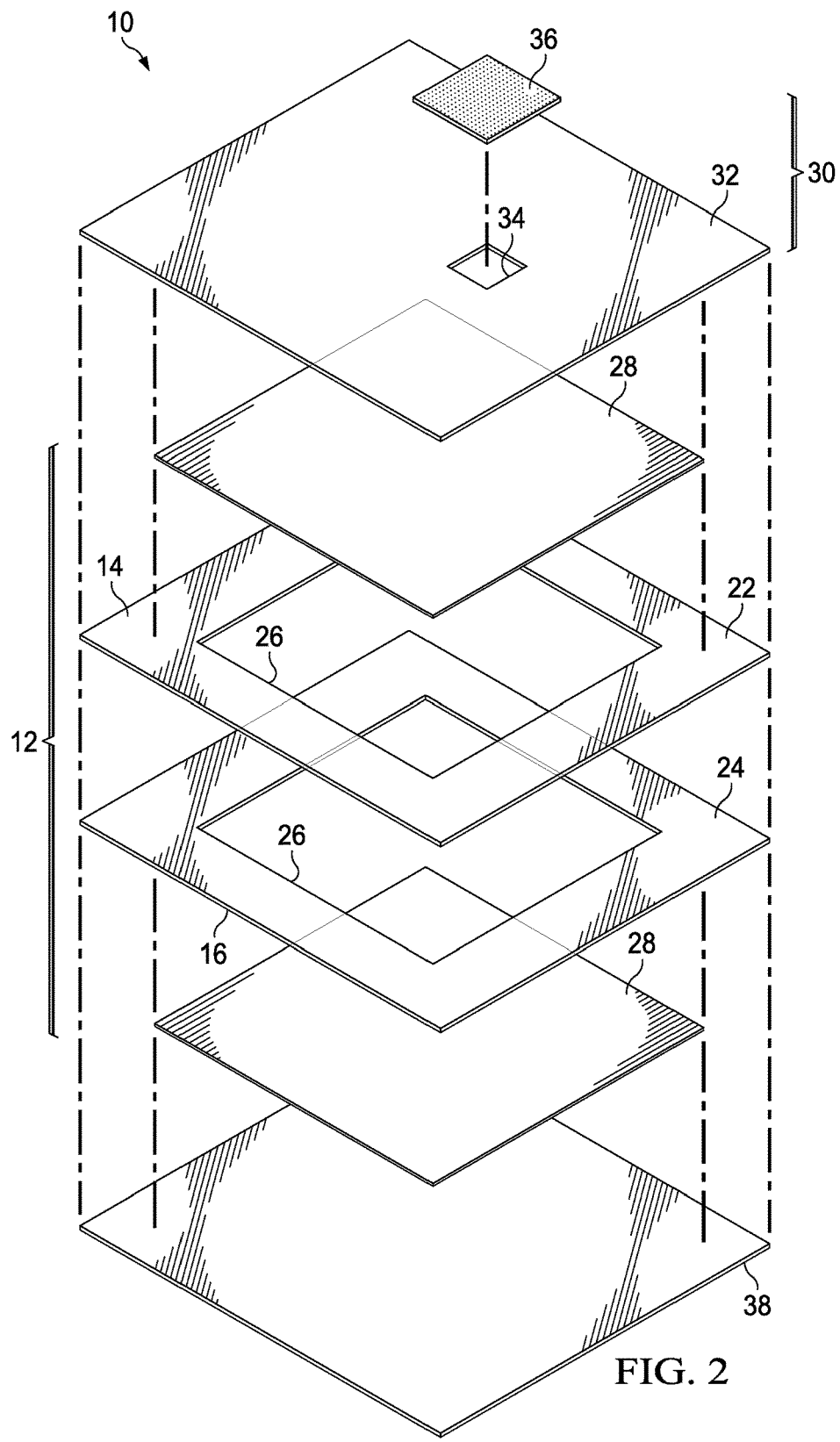
FIG. 2 is an exploded top and left perspective view of the cultivation bag assembly of FIG. 1.

In one application, an optional film layer 38 (FIG. 2) is provided with the bag assembly 10. The film layer 38 is gas impermeable and is not provided with any opening, such as the opening 34 of layer 32, so that water vapor and gases cannot readily pass through the material of the film. The film layer 38 may be formed from a thermoplastic film, such as the polyolefins of polypropylene or HDPE. The film layer 38 is sized and configured to overlay the entire surface of the water-vapor permeable layer 28 of the lower wall 16 to prevent the passage of gases to and from the permeable layer 28 through the film 38.

The film layer 38 may be releasably joined to the lower bag wall 16, as well. This may be achieved by utilizing different polyolefin materials or thermoplastic materials with different melting points for each of the film layer 38 and the lower film layer 24. In many instances, the film layer 38 will be the same or a similar material to the film layer 32 used for the bag overlay 30.

Figure 4:
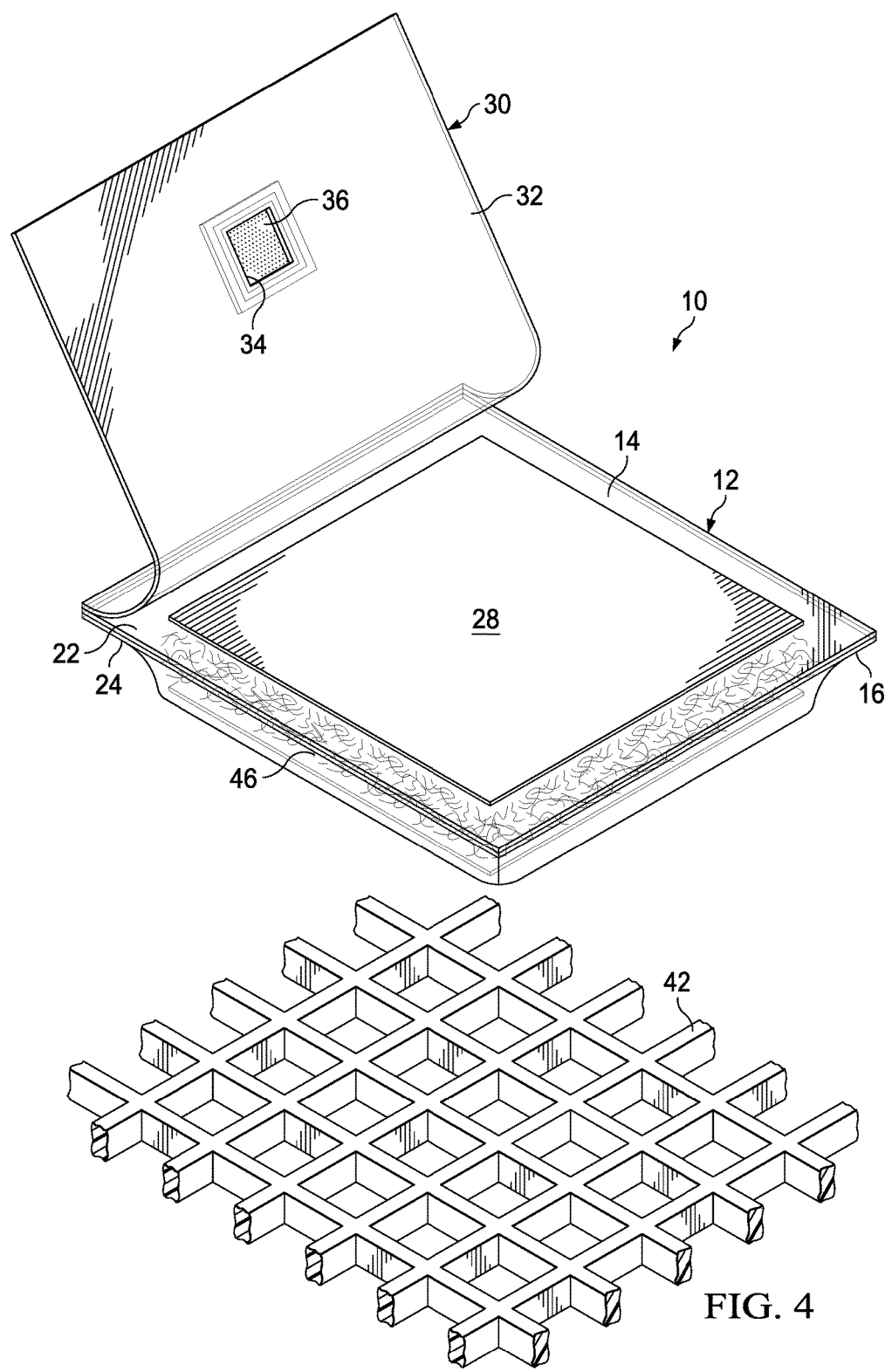
FIG. 4 is a top and left perspective view of the cultivation bag assembly of FIG. 1 shown with a bag wall overlay partially peeled away from the bag assembly and positioned over a grating to facilitate drying.

In other embodiments, the removable gas impermeable layer 38 is not used with the bag assembly 38. Whether the lower gas impermeable layer 38 is used or not may depend upon how the bag assembly 10 is used during cultivation. As shown in FIG. 1, the bag assembly 10 may be placed upon a solid shelf or support surface during cultivation, such as the support surface 40. The support surface 40 may be solid plastic, stainless steel, etc. In such instances, the gas impermeable layer 38 may not be necessary as the solid support surface 40 acts to effectively seal the lower permeable layer 28 of the lower wall 16 to prevent the passage of gases and water vapor to and from the lower permeable layer 28.

Where the bag assembly 10 is used over a non-solid or vented surface during cultivation, such as the grating 42 of FIG. 4, the use of a removable gas impermeable layer 38 prevents water vapor and gases from passing to and from the lower permeable layer 28.

Figure 3:
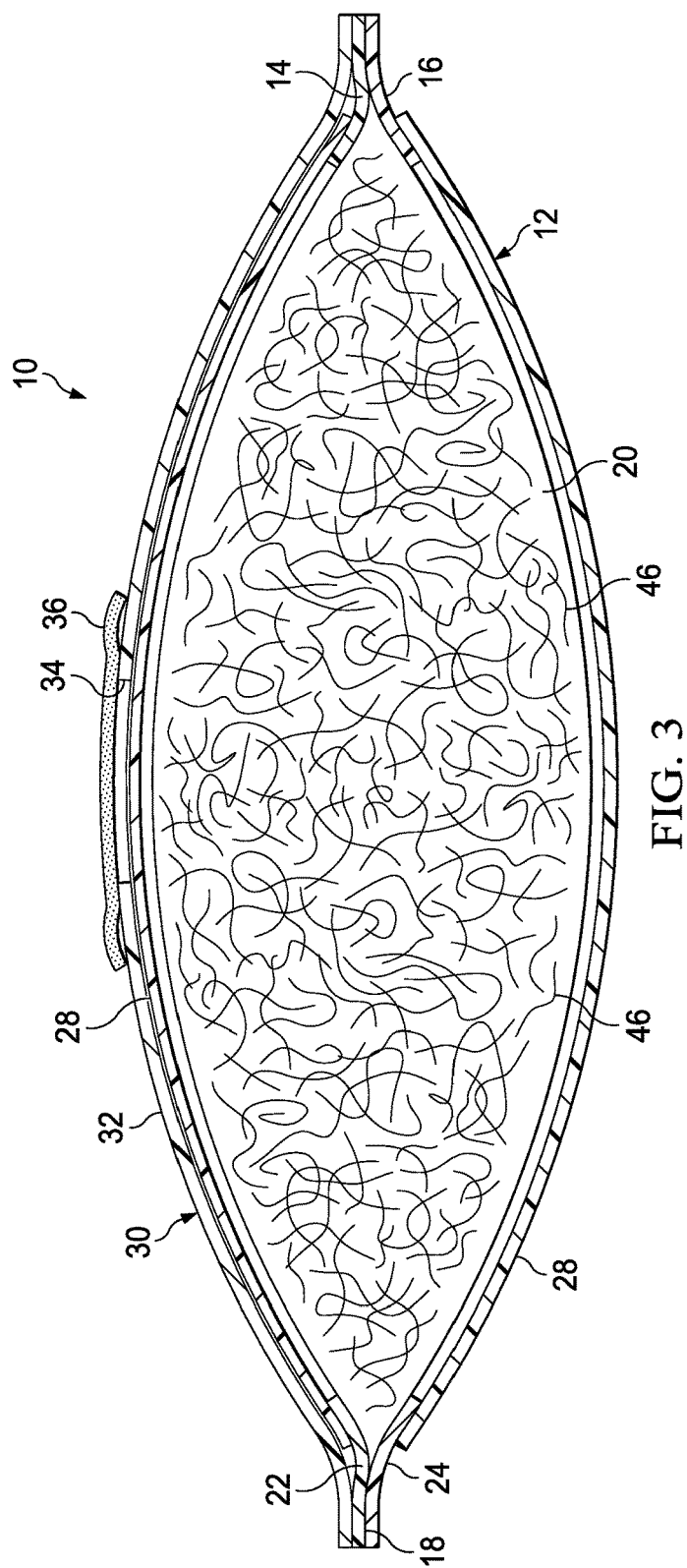
FIG. 3 is a cross-sectional view of cultivation bag assembly of FIG. 1 taken along the lines 3-3.

As shown in FIG. 1, one end of the bag assembly 10 may be open with the front side edges of the upper and lower walls 14, 16 not being joined together to define an opening 44 of the bag assembly 10. This allows for the introduction of a food substrate, along with microbes, fungi or other organisms, such as fungi mycelium, to be cultivated, such as shown at 46 of FIG. 3, into the bag interior 20. The food substrate is typically an organic material that provides nutrients and moisture for the cultivation of the desired microbe or organisms. The substrate may be wet or dry. One suitable type of substrate useful for the cultivation of fungi mycelium is wet rice. Other substrate materials may also be used, however, and may vary based upon the organism being cultivated.

The bag assembly 10, including any substrate, may be sterilized or fabricated under sterile conditions to prevent contamination of the cultivated organisms. If the materials can withstand heat sterilization, heat sterilization may be used. Heat sterilization may be used by heating the bag assembly 10 and/or its components, with or without any substrate, to a temperature of from 121° C. or higher to effectively kill any unwanted bacteria, viruses or other undesirable microorganisms.

Because components of the bag assembly 10 may be constructed of different thermoplastic materials, such as HDPE, which may have a lower melting point that would degrade the material if such high temperatures were used, other non-heat sterilization techniques may need to be used. This may include radiation, such as gamma radiation, or chemical sterilization. In such instances, the bag assembly 10, with or without any substrate, is subjected to radiation or sterilization chemicals to effectively sterilize the bag assembly and any substrate contained therein.

Once the bag assembly 10 and substrate are sterilized, pure microorganisms, fungi or other organisms to be cultivated are introduced into the interior 20 of the bag 12 through opening 44. This may be done in sterile or clean room conditions to avoid any contamination of the materials. The opening 44 is then sealed, such as by heat or ultrasonic welding the front side edges of the upper and lower film layers 22, 24 so that the opening 44 is sealed shut. The bag assembly 10 and its contents may then be agitated to thoroughly mix the contents within the bag assembly.

With the cultivation bag assembly 10 sealed and the contents mixed, the bag assembly and its contents are placed in an environment (e.g., temperature, humidity, light, etc.) suitable for growing and cultivation. As discussed, the bag assembly 10 may initially rest on a solid surface or shelf during cultivation, such as the surface 40 (FIG. 1), so that the use of the impermeable layer 38 is unnecessary. In certain instances, however, the bag assembly 40 may rest on a ventilated surface or grating, such as the grating 42 (FIG. 4). Here, it may be desirable to use the removable impermeable layer 38 over the lower wall 16 to prevent premature drying.

The bag overlay 30 (as well as the optional impermeable layer 38) prevents premature drying, as well as allows the passage of air and oxygen and carbon dioxide through the filter patch 36 so that optimal cultivation conditions are maintained within the bag interior 20 during their growth.

When the cultivated organisms are ripe, which is typically after all of the substrate has been consumed by the cultivated organism, the bag contents are dried. As discussed earlier, in prior art methods, this would typically occur by emptying the contents of the cultivation bag into a separate drying bag. With the bag assembly 10 of the invention, however, this is not needed as both cultivation and drying can be accomplished using the same bag assembly.

To dry the bag assembly contents, the bag overlay 30 is peeled away and removed from the upper wall 14, such as shown in FIG. 4. The low bond strength between the film layer 32 and the upper film layer 22 of the upper wall 14 allows the overlay 30 to be released and readily removed with a relatively low degree of effort. This uncovers the water-vapor permeable layer 28 so that water vapor can readily evaporate and escape from the interior 20 of the bag 12 through the large area provided by the large permeable layer 28. If the bag assembly 10 has been resting on a grating or vented support surface, such as the grating 42 (FIG. 4), any lower impermeable layer 38 (FIG. 2) may be removed, as well. Thus, water vapor may pass through the lower water-vapor permeable layer 28 of the bottom wall 16, as well as through the permeable layer 28 of the upper wall 14, to facilitate drying. In many applications, the drying may be conducted with heating and/or under vacuum within a vacuum chamber to speed up drying.

In cases where the bag assembly 10 and its contents are cultivated while resting on a solid surface, such as the support surface 40 (FIG. 1), without the use of the impermeable layer 38, the bag assembly 10 may be transferred and placed on a ventilated surface, such as the grating 42 for drying. The larger filter layers 28 allow faster drying while retaining the cultivated contents within the bag 12.

After drying, the bag assembly 10 and its contents may be agitated to break the materials within into smaller particles. The bag assembly 10 and its contents may then be packaged, shipped and/or stored for later use as biopesticide or biological agent that can be spread on agricultural plots for growing crops for controlling pests, weeds or for use as a fertilizer, as described earlier. The bag assembly 10 is made of durable materials so that it can be used for shipping and storage without having to unseal and remove the contents and placing them in a different bag prior to use.

Figure 5:
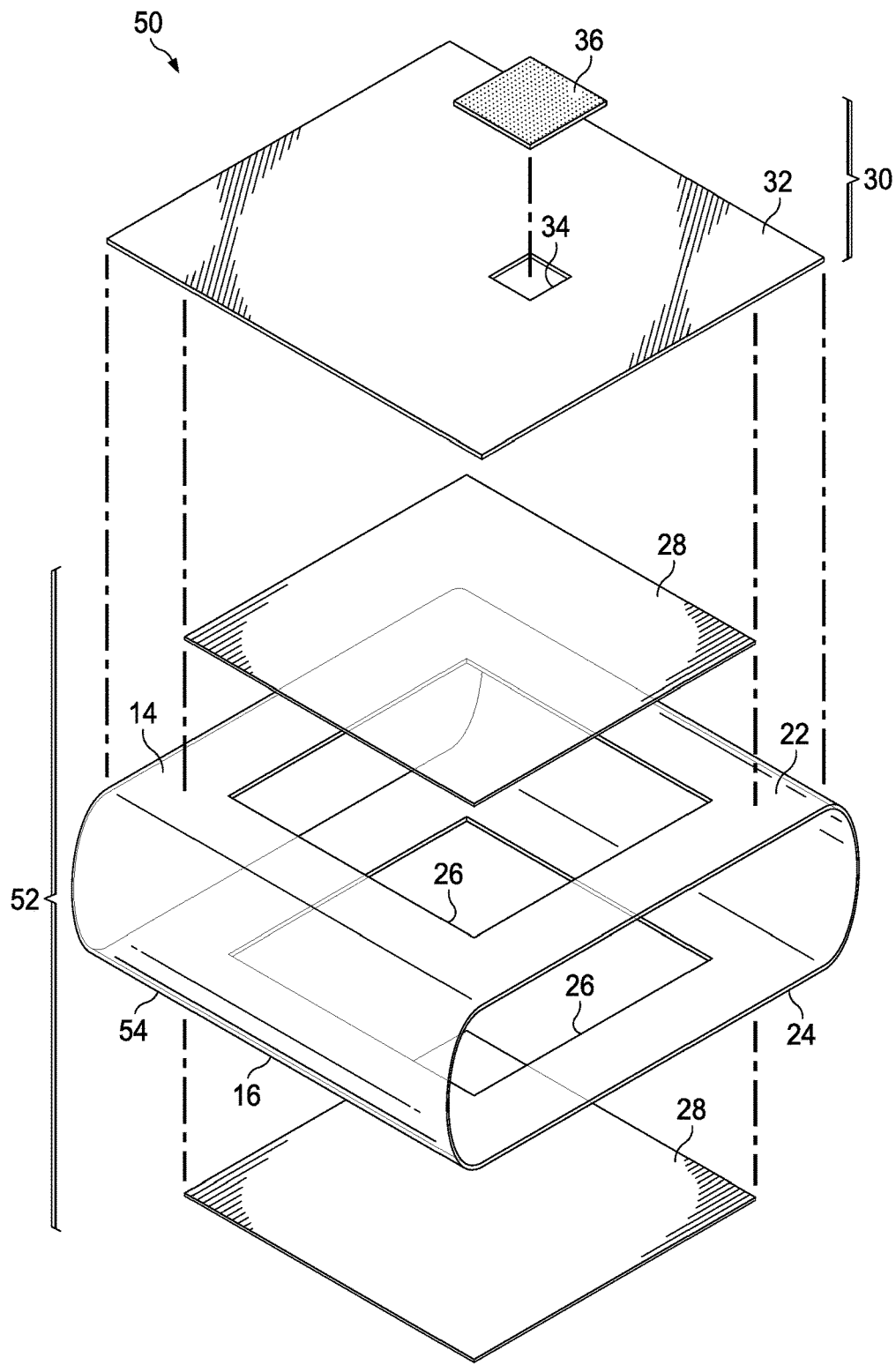
FIG. 5 is an exploded top and left perspective view of an alternate embodiment of a cultivation bag assembly of FIG. 1 with a bag of the bag assembly being formed from a single film layer in a tubular configuration.

FIG. 5 shows an alternate construction of a cultivation bag assembly 50. The bag assembly 50 is constructed similarly to bag assembly 10, with similar components labeled with the same reference numeral. The bag assembly 50 includes a bag 52 that is formed in part from a single layer of film 54. The single film 54 is configured in a tubular configuration, as shown. This may be achieved by joining the single film layer 54 along a single longitudinal left or right side edge to form a seam. In many instances, however, the tubular film 54 will be extruded or otherwise formed as a tube during fabrication, so that there is no joint or seal is present along the left and right side edge, with the film layer 54 being a continuous seamless piece of material. This facilitates strengthening of the bag 52 so that there are no seals or joints along the left and right side edges, making the bag 52 less prone to failure. The opposite upper and lower faces of the tubular film 54 constitute the upper and lower film layers 22, 24 to form the walls 14, 16. The remainder construction of the bag assembly 50, including the bag wall overlay 30, is generally the same as that for the bag assembly 10, previously described.

In a variation of the embodiment of FIG. 5, where the permeable material 28 forms both of the bag walls 14, 16, without the use of any film layer, as discussed earlier, the permeable material 28 may be a single layer of material, such as non-woven polyolefin fiber material, that is configured in tubular configuration. This may be achieved by joining the single layer of permeable material along a single longitudinal left or right side edge to form a seam. In many instances, however, the layer of permeable material will be formed as a tube during fabrication, so that there is no joint or seal present along the left and right side edge, with the tubular-shaped permeable layer being a continuous seamless piece of material.

Figure 6:
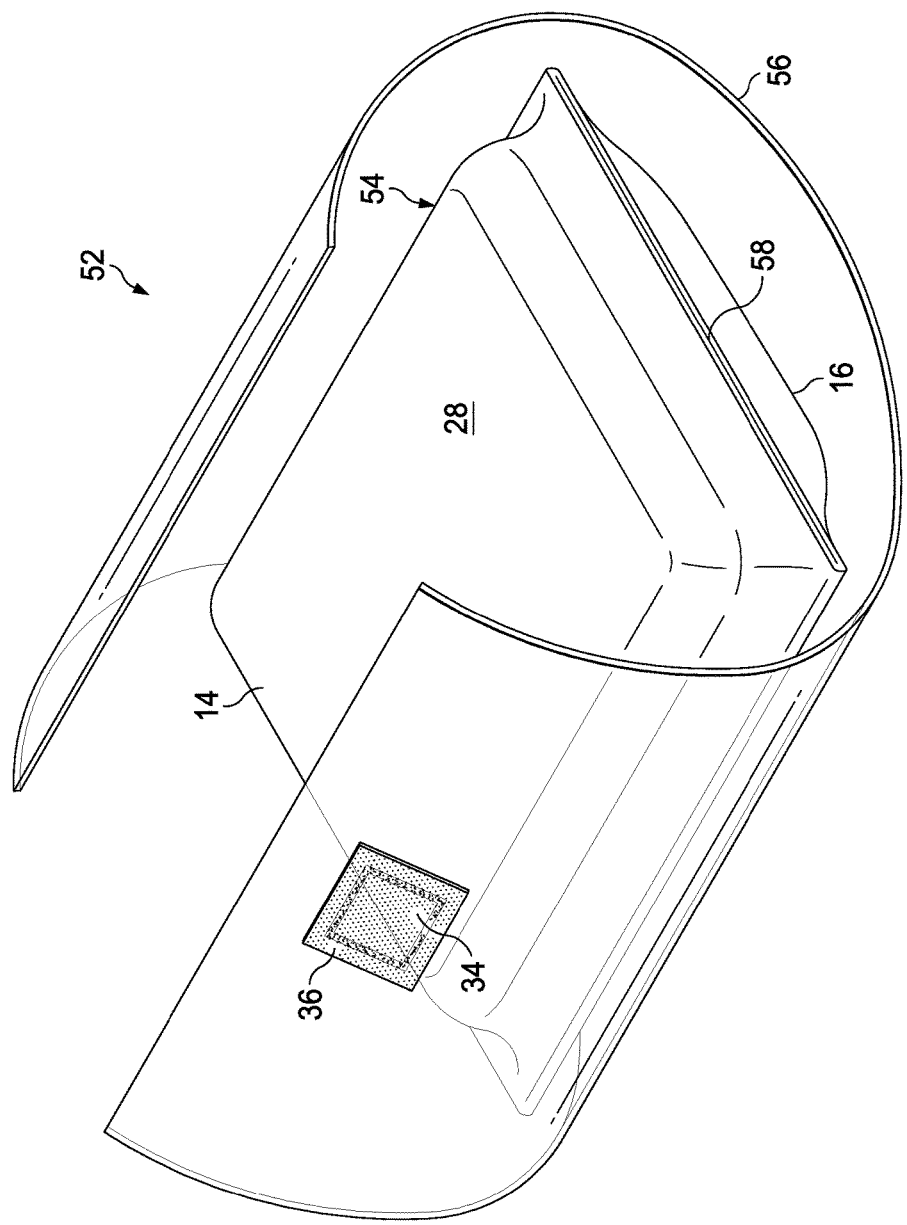
FIG. 6 is a top and left perspective view of another alternate embodiment of cultivation bag assembly with a bag wall overlay of the bag assembly being wrapped around a prefilled drying bag of the bag assembly.

FIG. 6 shows still another variation of a bag assembly 52. The bag assembly 52 is constructed similarly to bag assemblies 10 and 50, with similar components labeled with the same reference numeral. The bag assembly 52 includes a drying bag 54 that may be constructed similarly to the bag 12 of bag assemblies 10 and 50. In the embodiment of FIG. 6, the walls 14 and 16 of the drying bag 54 are formed entirely of water-vapor permeable layers 28, such as the Tyvek® material previously described. Alternatively, the bag 54 could be constructed similarly to the bag 12 of FIG. 1, including the film layers 22, 24.

A bag wall overlay layer 56 of the bag assembly 52 is wrapped around the bag 54. The layer 56 may be a single sheet of material that is an oversized or large layer so that it can be wrapped around all surfaces and sides of the bag 54, with the entire bag 54 being encompassed by the overlay layer 56. In many instances, the substrate and material to be incubated may already be introduced into and contained within the bag 54, with the end of the prefilled bag 54 already being sealed, such as at seal 58, when the bag wall overlay 56 is added. This may be done under sterile conditions.

The bag overlay 56 is gas impermeable and may be the same material as the film material 32, previously described. The edges and ends of the layer 56 may be joined and sealed together to provide an air or gas tight seal around the bag 54. As with the overlay 32, previously described, an opening 34 and incubation filter patch 36 are provided on the layer 56, which overlays the permeable layer 28 of the drying bag 54 to allow passage of gases therethrough, but keeps unwanted contaminants from entering the bag assembly 52.

After incubation, the bag overlay 56 may be removed from the bag 12 for drying, as has been previously described.

Figure 7:
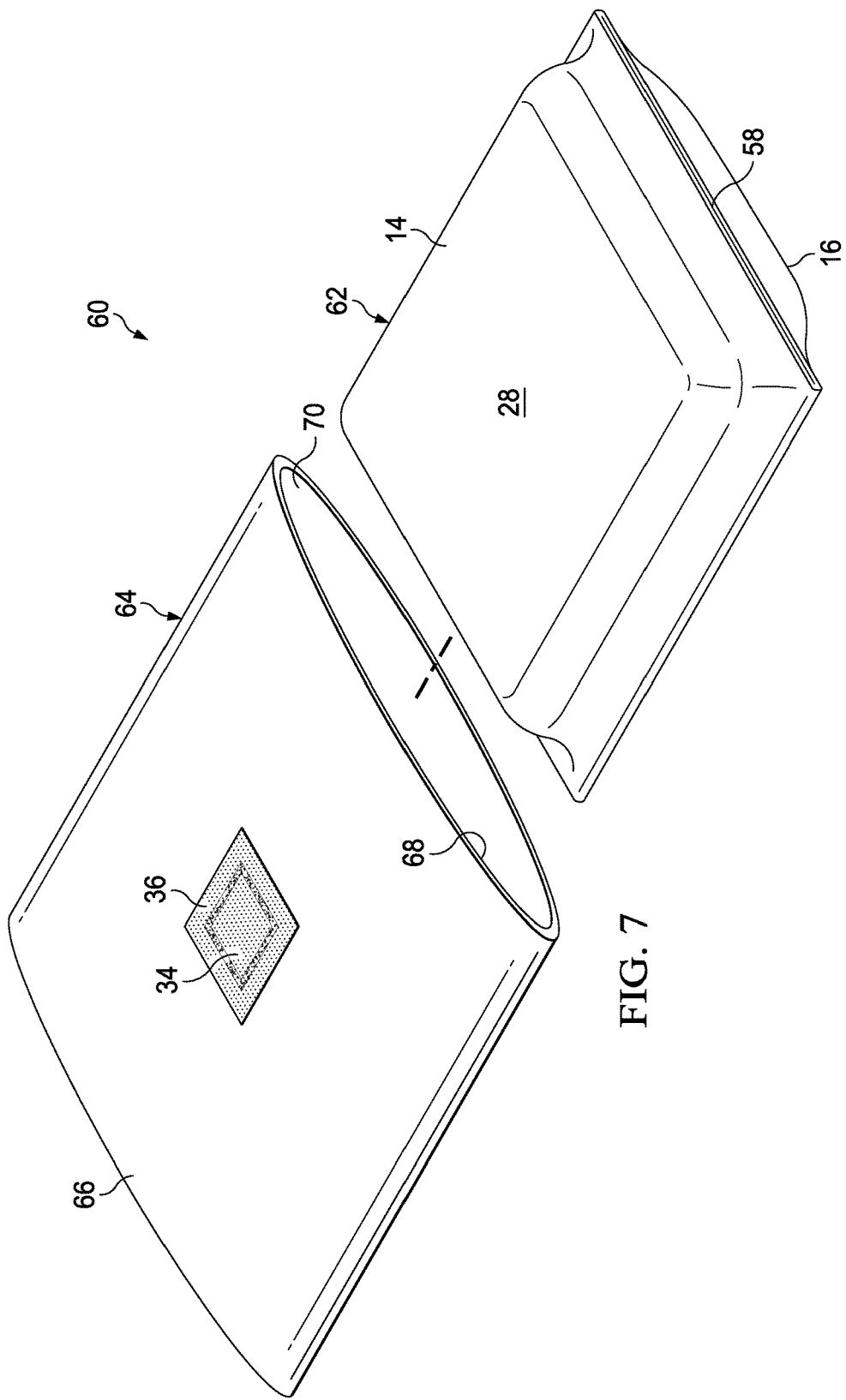
FIG. 7 is a top and left perspective view of still another alternate embodiment of a cultivation bag assembly with a bag wall overlay of the bag assembly being formed as a preformed bag into which a prefilled drying bag is introduced and sealed therein.

Referring to FIG. 7, another variation of a bag assembly 60 is shown. The bag assembly 60 is constructed similarly to bag assemblies 10, 50, and 52, with similar components labeled with the same reference numeral. The bag assembly 60 includes a drying bag 62, which may be the same or similar to the bags 12 and 54 of bag assemblies 10, 50, 52. Like the bag 54 of the embodiment of FIG. 6, the walls 14 and 16 of the drying bag 62 of bag assembly 60 are shown formed entirely of water-vapor permeable layers 28, such as the Tyvek® material previously described. Alternatively, the bag 62 could be constructed similarly to the bag 12 of FIG. 1, including the film layers 22, 24. The drying bag 62 may be prefilled with the substrate and material to be incubated.

A bag wall overlay layer 64 of the bag assembly 52 is formed as a separate preformed bag 66. The preformed bag 66 of the bag overlay 64 is formed from one or more gas impermeable film layers, which may be the same material as the film material 32, previously described. The edges of the film layer or layers of the bag 66 may be joined and sealed together along the sides to provide an air or gas tight seal around the drying bag 66. One side of the bag 66 is left unsealed to leave an opening 68 to access the interior 70 of the bag 66.

As with the overlay 32, previously described, an opening 34 and incubation filter patch 36 are also provided on the layer 64, which overlays the permeable layer 28 of the drying bag 62 to allow passage of gases therethrough, but keeps unwanted contaminants from entering the bag assembly 60.

The material to be incubated may already be introduced into the bag 62, with the end of the bag 62 already sealed, such as at seal 58. The bag 62 is introduced into the bag 62 through the opening 68 so that it rests within the interior 70 of bag 64. This may be done under sterile conditions. The opening 68 is then closed and sealed, such as with heat or ultrasonic welding, or with adhesive.

After incubation, the bag 64 may be opened and the drying bag 62 may be removed from the bag 64 for drying, as has been previously described.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

I claim:

1. A cultivation bag assembly for the cultivation of microbes, fungi and other organisms comprising:
   a bag having first and second walls joined along side edges to define a bag interior for containing a food substrate and an organism to be cultivated, at least one of the first and second walls being constructed of a layer of water-vapor permeable material to allow the passage of water vapor therethrough; and a bag wall overlay layer formed from gas impermeable layer that is releasably coupled to the bag, wherein the overlay layer overlays the layer of water-vapor permeable material to prevent the passage of gases therethrough, the bag wall overlay layer having an opening with a gas filter patch covering the opening to allow the passage of oxygen and carbon dioxide gases through the gas filter patch to and from ambient air to facilitate incubation of the organism within the interior of the bag, and wherein the bag wall overlay layer is removable from the bag to allow water vapor to pass through the layer of water-vapor permeable material to ambient air facilitate drying of the bag contents after incubation is complete.

2. The bag assembly of claim 1, wherein:
both first and second walls are constructed of a layer of water-vapor permeable material.

3. The bag assembly of claim 1, wherein:
the at least one of the first and second walls is formed from a polyolefin film layer having a central opening, and wherein the layer of water-vapor permeable material is joined to the polyolefin film layer to cover the central opening.

4. The bag assembly of claim 3, wherein
the layer of water-vapor permeable material is constructed from a non-woven polyolefin fiber material.

5. The bag assembly of claim 3, wherein:
the bag and bag wall overlay are each formed from different polyolefin materials.

6. The bag assembly of claim 5, wherein:
one of the bag and bag wall overlay is formed from polypropylene and the other is formed from high density polyethelene (HDPE).

7. The bag assembly of claim 1, wherein:
the bag overlay is releasably coupled to the bag by one of an adhesive layer and heat welding.

8. The bag assembly of claim 1, wherein:
the bag is constructed at least in part from a single film layer having a tubular configuration.

9. The bag assembly of claim 1, wherein:
the water-vapor permeable material has a perm rating of from 5 or greater.

10. A cultivation bag assembly for the cultivation of microbes, fungi and other organisms comprising:
a bag having first and second walls joined along side edges to define a bag interior for containing a food substrate and an organism to be cultivated, at least one of the first and second walls being formed from a polyolefin film layer having a central opening, and wherein a layer of water-vapor permeable material is joined to the at least one of the first and second walls to cover the central opening to allow the passage of water vapor therethrough; and a bag wall overlay layer formed from a gas impermeable film layer of a different polyolefin that is releasably coupled to at least one of the first and second walls, wherein the overlay layer overlays the layer of water-vapor permeable material to prevent the passage of gases therethrough, the bag wall overlay layer having an opening with a gas filter patch covering the opening to allow the passage of oxygen and carbon dioxide gases through the gas filter patch to and from ambient air to facilitate incubation of the organism within the interior of the bag, and wherein the bag wall overlay layer is removable from the bag to allow water vapor to pass through the layer of water-vapor permeable material to ambient air to facilitate drying of the bag contents after incubation is complete.

11. The bag assembly of claim 10, wherein:
the bag wall overlay is releasably coupled to the bag by heat welding, and wherein the different polyolefin materials have a sufficient low bonding strength after heat welding to facilitate the releasbility of the bag wall overlay from the bag.

12. The bag assembly of claim 11, wherein:
one of the bag and bag wall overlay is formed from polypropylene and the other is formed from high density polyethelene (HDPE).

13. The bag assembly of claim 10, wherein:
both the first and second walls are formed from a polyolefin film layer having a central opening, and wherein a layer of water-vapor permeable material is joined to each of the first and second walls to cover the central openings to allow the passage of water vapor therethrough.

14. The bag assembly of claim 10, wherein:
the layer of water-vapor permeable material is constructed from a non-woven polyolefin fiber material.

15. The bag assembly of claim 10, wherein:
the bag is constructed at least in part from a single film layer having a tubular configuration.

16. The bag assembly of claim 10, wherein:
the water-vapor permeable material has a perm rating of from 5 or greater.

17. A method of forming a cultivation bag assembly for the cultivation of microbes, fungi and other organisms comprising:
forming a bag having first and second walls joined along side edges to define a bag interior for containing a food substrate and an organism to be cultivated, at least one of the first and second walls being constructed of a layer of water-vapor permeable material to allow the passage of water vapor therethrough; and releasably coupling a bag wall overlay layer formed from gas impermeable layer to the bag, wherein the overlay layer overlays the layer of water-vapor permeable material to prevent the passage of gases therethrough, the bag wall overlay layer having an opening with a gas filter patch covering the opening to allow the passage of oxygen and carbon dioxide gases through the gas filter patch to and from ambient air to facilitate incubation of the organism within the interior of the bag, and wherein the bag wall overlay layer is removable from the bag to allow water vapor to pass through the layer of water-vapor permeable material to ambient air facilitate drying of the bag contents after incubation is complete.

18. The method of claim 17, wherein:
the bag and bag wall overlay are each formed from different polyolefin materials, and wherein the bag wall overlay is releasably coupled to the bag by heat welding, the different polyolefin materials having a sufficient low bonding strength upon heat welding to facilitate the releasbility of the bag wall overlay from the bag.

19. The method of claim 18, wherein:
one of the bag and bag wall overlay is formed from polypropylene and the other is formed from high density polyethelene (HDPE).

20. The method of claim 17, wherein:
the bag assembly is a sterilized by gamma irradiation.

* * * * *